(12) United States Patent
Lathrop et al.

(10) Patent No.: US 10,149,694 B2
(45) Date of Patent: Dec. 11, 2018

(54) ENERGY BALANCE MECHANISM FOR FLEXURE JOINT

(71) Applicant: Vanderbilt University, Nashville, TN (US)

(72) Inventors: Ray A. Lathrop, Nashville, TN (US); Robert J. Webster, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 1126 days.

(21) Appl. No.: 14/484,716

(22) Filed: Sep. 12, 2014

(65) Prior Publication Data

US 2015/0080908 A1 Mar. 19, 2015

Related U.S. Application Data

(60) Provisional application No. 61/877,391, filed on Sep. 13, 2013.

(51) Int. Cl.
*A61B 17/00* (2006.01)
*A61B 17/29* (2006.01)
*A61B 90/50* (2016.01)
*A61B 34/30* (2016.01)

(52) U.S. Cl.
CPC .............. *A61B 17/29* (2013.01); *A61B 34/30* (2016.02); *A61B 2017/003* (2013.01); *A61B 2090/5025* (2016.02)

(58) Field of Classification Search
CPC .... A61B 17/29; A61B 2017/003; A61B 34/30
USPC ......... 606/1, 41, 51, 52, 113, 139, 167, 170, 606/185, 205, 209
See application file for complete search history.

(56) References Cited

U.S. PATENT DOCUMENTS

| | | | |
|---|---|---|---|
| 4,315,650 A | 2/1982 | Yoshida | |
| 5,286,228 A | 2/1994 | Lee et al. | |
| 5,468,250 A | 11/1995 | Paraschac et al. | |
| 5,599,151 A | 2/1997 | Daum et al. | |
| 5,813,813 A | 9/1998 | Daum et al. | |
| 6,322,578 B1 | 11/2001 | Houle et al. | |

(Continued)

FOREIGN PATENT DOCUMENTS

| | | |
|---|---|---|
| CN | 1438097 | 8/2003 |
| CN | 2917558 | 7/2007 |

(Continued)

OTHER PUBLICATIONS

Radius Surgical System surgical tool, publicly available prior to Apr. 29, 2011.

(Continued)

*Primary Examiner* — Vy Bui
(74) *Attorney, Agent, or Firm* — Michael Best & Friedrich LLP

(57) ABSTRACT

Systems and method are described for counterbalancing the force required to deform a flexure joint. The system includes an elastically deformable flexure joint, a control joint, and an energy balance system. The control joint is mechanically linked to the flexure joint such that movement of the control joint causes a corresponding deformation of the flexure joint. The energy balance system provides a spring force to aid movement of the control joint and to overcome an elastic force required to deform the flexure joint.

16 Claims, 7 Drawing Sheets

(56) References Cited

U.S. PATENT DOCUMENTS

| | | | |
|---|---|---|---|
| 7,090,637 | B2 | 8/2006 | Danitz et al. |
| 7,338,513 | B2 * | 3/2008 | Lee ..................... A61B 17/29 606/139 |
| 7,372,229 | B2 | 5/2008 | Farritor et al. |
| 7,373,219 | B2 | 5/2008 | Nowlin et al. |
| 7,386,365 | B2 | 6/2008 | Nixon |
| 7,404,716 | B2 | 7/2008 | Gregorio et al. |
| 7,410,483 | B2 | 8/2008 | Danitz et al. |
| 8,617,203 | B2 | 12/2013 | Stefanchik et al. |
| 2006/0020288 | A1 | 1/2006 | Leonard |
| 2007/0225754 | A1 | 9/2007 | Measamer et al. |
| 2008/0065106 | A1 | 3/2008 | Larkin |
| 2008/0071288 | A1 | 3/2008 | Larkin et al. |
| 2008/0071290 | A1 | 3/2008 | Larkin et al. |
| 2008/0071291 | A1 | 3/2008 | Duval et al. |
| 2008/0140129 | A1 | 6/2008 | Dalton |
| 2010/0198253 | A1 | 8/2010 | Jinno et al. |
| 2010/0298864 | A1 | 11/2010 | Castro |
| 2011/0106145 | A1 | 5/2011 | Jeong |

FOREIGN PATENT DOCUMENTS

| | | |
|---|---|---|
| CN | 11011292 | 8/2007 |
| WO | 2008041227 | 4/2008 |

OTHER PUBLICATIONS

Novare RealHand surgical tool, publicly available prior to Apr. 29, 2011.

Neuroarm surgical system, http://www.neuroarm.org/, publicly available prior to Apr. 29, 2011.

ZEUS Robotic Surgical System, https://web.archive.org/web/20030205054707/http://computermotion.com/zeus.html, publicly available prior to Apr. 29, 2011.

QuadPort multi-instrument access port, http://www.advancedsurgical.ie/QuadPort/Default.544.html, publicly available prior to Apr. 29, 2011.

Triport product, http://www.advancedsurgical.ie/TriPort_15/Default.595.html; information available prior to Apr. 29, 2011.

AESOP 3000 System, https://web.archive.org/web/20030203213235/http://computermotion.com/aesop.html, publicly available prior to Apr. 29, 2011.

ROBODOC Surgical Robot, http://www.robodoc.com/professionals.html, publicly available prior to Apr. 29, 2011.

Bhaheetharan, Sujan et al., "Minimally Invasive Surgery Tool," http://homepages.cae.wisc.edu/~bme200/robotic_arm_fall05/reports/BME_mid_sem_report.pdf (Oct. 18, 2005).

Humphries, Courtney, "New Tools for Minimally Invasive Surgery," MIT Technology Review (Aug. 9, 2006).

Children's Hospital Boston, "Minimally Invasive Heart Surgery Research Wins $5 million NIH Award," http://www.childrenshospital.org/newsroom/Site1339/mainpageS1339P1sublevel340.html (Sep. 5, 2007).

Jaspers, Joris, "Cheaper and Simpler Keyhole Surgery," Delft University of Technology (Mar. 21, 2006) http://www.tudelft.org/en/current/latest-news/article/detail/kijkoperaties-goedkoper-en-eenvoudiger/.

Diks, J. et al., "The mechanical master-slave manipulator: an instrument improving the performance in standardized tasks for endoscopic surgery," Surgical Endoscopy, vol. 21, No. 6 1025-1031 (Jun. 2007).

"Startup's device may change surgery," The News & Observer (Jan. 8, 2008) http://satellite.tmcnet.com/news/2008/01/08/3200080.htm.

"Trends in the noninvasive and minimally invasive medical device market," BCC Research (Jun. 2006) http://www.surgicenteronline.com/articles/751feat3.html.

Ethicon Endo-Surgery Inc., http://www.ethiconendo.com/dtcf/pages/innovative_products.htm; information available prior to Apr. 29, 2011.

Mectra Labs, Inc., About Mectra http://www.mectralabs.com/aboutMectra.cfm; information available prior to Apr. 29, 2011.

* cited by examiner

ENERGY BALANCE MECHANISM FOR FLEXURE JOINT

RELATED APPLICATIONS

This application claims the benefit of U.S. Provisional Patent Application No. 61/877,391, filed Sep. 13, 2013, the entire contents of which are incorporated herein by reference.

BACKGROUND

The present invention relates to flexure mechanism such as, for example, a flexure joint of a surgical tool. Because a flexure joint bends by elastic deformation of a structure, force is required to maintain the position of a flexure joint and to prevent it from returning to its original, non-deformed shape.

SUMMARY

Joints that involve elastic deformation of a structure in order to operation (e.g., "flexure joints") can be used in various applications including, for example, robotic and manually actuated surgical arms, manipulators, flexible scopes, and catheters. The elastic deformation of the structure causes that joints/structure to act like a compressed spring. This spring energy is typically felt by either the user or servo motor as a constant force pushing back against the controls and trying to return the joint/structure to its unbent state. Because of the constant force needed to actuate and hold the continuum joint in a deformed position, flexure joints alone are not practical for use with manual tool.

In one embodiment, the invention provides a mechanical energy balance of a flexure joint. This balance mechanism balances the joint's potential energy such that the user/servo motor no longer needs to resist a constant restoring force. In some embodiments, the flexure joint includes a continuum joint integrated into a dexterous laparoscopic manipulator such as, for example, an elbow joint in a surgical tool. In some embodiments, the energy balance mechanism includes a joint, a control handle, and a spring mechanism. The joint is a flexure joint that elastically stores energy when deformed. The control handle moves above the joint and controls the movement of the joint. The force required to move the control handle is mechanically linked to the joint. The spring mechanism is attached to the control handle and provides energy balance.

In another embodiment, the invention provides a tool including an elastically deformable flexure joint, a control joint, and an energy balance system. The control joint is mechanically linked to the flexure joint such that movement of the control joint causes a corresponding deformation of the flexure joint. The energy balance system provides a spring force to aid movement of the control joint and to overcome an elastic force required to deform the flexure joint.

In yet another embodiment, the invention provides a surgical tool that includes a hollow shaft and an end effector coupled to the distal end of the hollow shaft by an elastically deformable flexure joint. A joint control arm is coupled to the proximal end of the hollow shaft by a control joint. The control joint is mechanically coupled to the flexure joint such that movement of the control joint causes a corresponding deformation of the flexure joint. An energy balance system provides a spring force that aids movement of the control joint and overcomes an elastic force required to deform the flexure joint.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
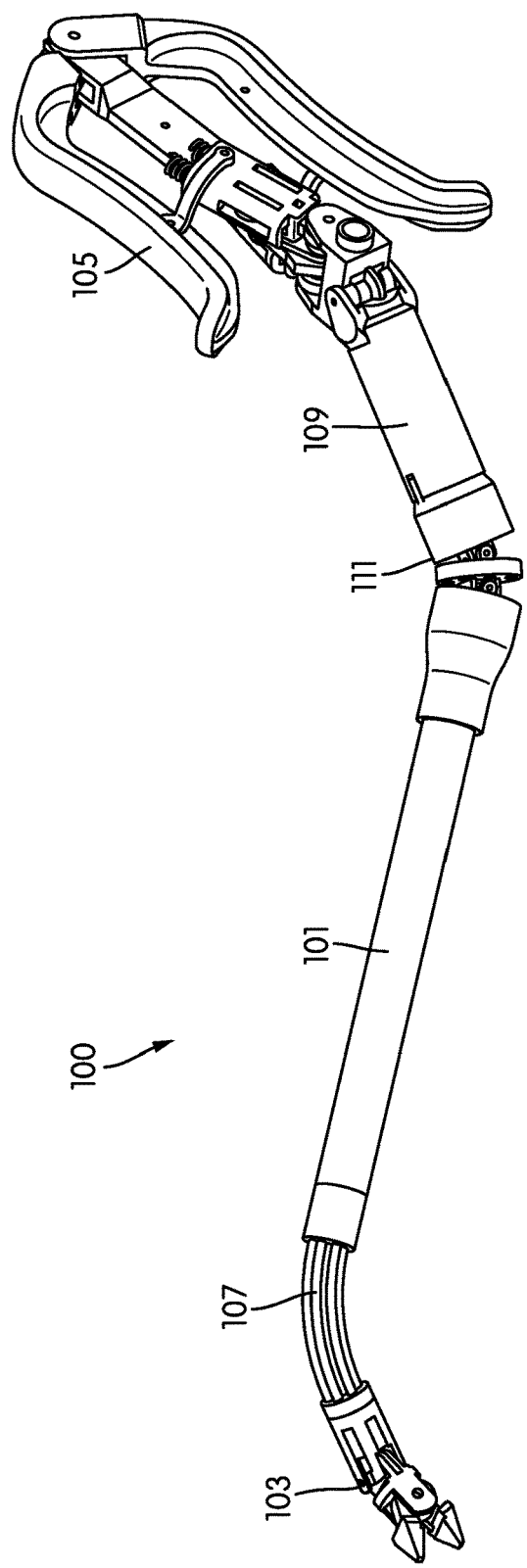
FIG. 1 is a perspective view of a manually actuated surgical tool including a flexure joint.
Figure 3:
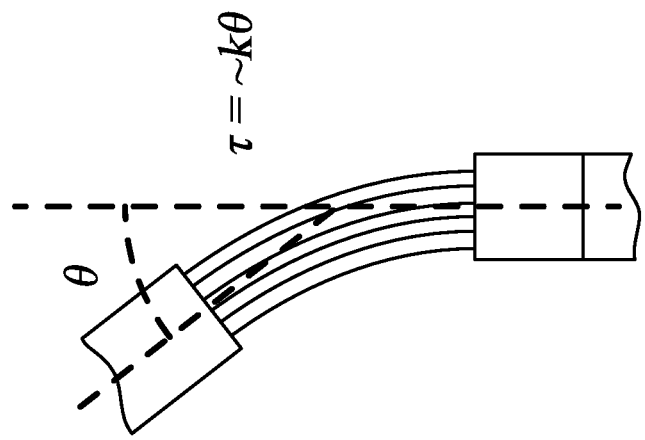
FIG. 3 is a detailed view of the flexure joint of the surgical tool of FIG. 1 in a deformed state.

FIG. 1 illustrates a manually operated laparoscopic manipulator. The surgical tool 100 includes a hollow shaft 101 with a gripper tool 103 positioned at the distal end. An end effector control handle 105 is used to control the orientation and operation of the gripper tool 103. The control handle 105 can be tilted in two degrees of freedom to control the angle of the gripper 103 (i.e., a "wrist joint") and the handles of the control handle 105 can be squeezed together to open and close the gripper 103.

In addition to a mechanical wrist joint incorporated into the gripper structure 103 itself, the tool 100 includes a flexure joint 107 positioned between the gripper 103 and the hollow shaft 101. The flexure joint 107 as described in further detail below includes a deformable portion of a continuum shaft. The bend and shape of the flexure joint 107 is controlled by moving the flex joint control handle 109. In particular, the joint control handle 109 is bent relative to the shaft 101 at control joint 111. Due to the structure of the continuum shaft, the flexure joint 107 bends in response to a bend at the control joint 111 such that the base of the gripper 103 remains substantially parallel with the flex joint control handle 109. The control joint 111 allows the flex joint control handle 109 to move with two degrees of freedom. Therefore, the flexure joint 107 is also capable of moving with two degrees of freedom.

Figure 2:
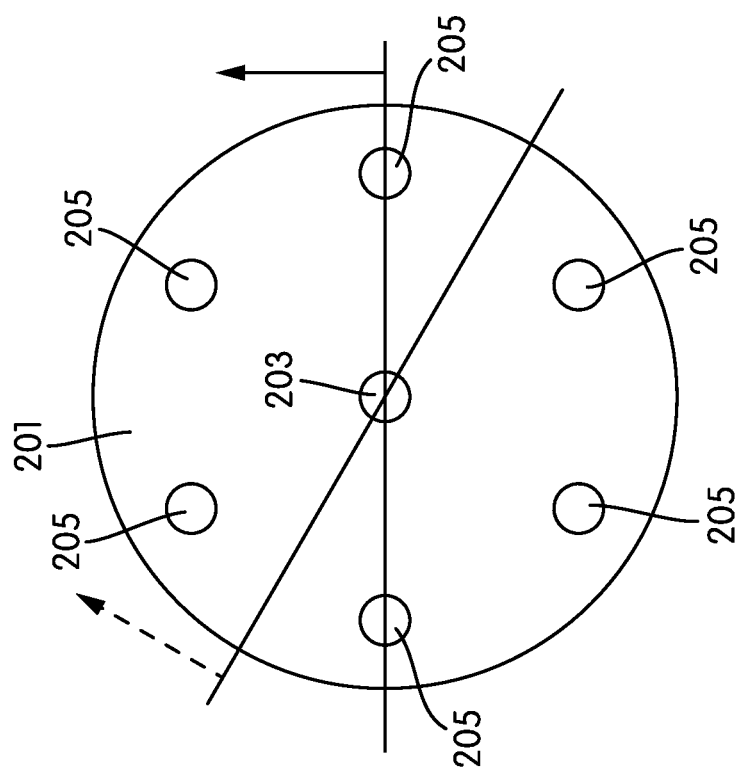
FIG. 2 is a cross-sectional view of the flexure joint of the surgical tool of FIG. 1.

FIG. 2 further illustrates the details of the continuum shaft that makes up the flexure joint 107 from FIG. 1. The continuum shaft includes a plurality of discs 201 arranged along the length of the continuum shaft. The continuum shaft runs from the control handle 109 through the hollow shaft 101 and extends to the base of the gripper 103. Each disc is fixedly joined to the other discs by a backbone that connects to the center of each disc 201 at 203. A plurality of flexible tubes also extend through each disc at points 205. However, these secondary tubes are only affixed to the end discs of the continuum shaft. Therefore, they can be pushed and pulled through holes 205 to control the shape of the continuum shaft. Each disc also includes one or more access ports (not pictured) that allow control devices to extend from the end effector control handle 105 to the gripper 103 and to control the operation of the gripper 103.

When the control joint 111 is bent in a first direction, it pushes the secondary tubes on the right side of the continuum shaft and pulls the secondary tubes on the left side fo the continuum shaft. Because the hollow shaft 101 (of FIG. 1) holds the continuum shaft straight, the movement of the control joint 111 and the corresponding pushing and pulling of the secondary tubes causes the flexure joint to bend to the left as shown in Fig In this example, each secondary tube is a hollow structure formed of a nitonol material. Each secondary tube has a 1.8 mm outer diameter and a 1.4 mm inner diameter. Movement of the control joint 111 causes a circular bend arc at the flexure joint 107 and the secondary tubes exhibit negligible stretching. The disc 201 has a diameter of 6 mm and the length of the flexure joint is 15 mm along the centerline. The difference between bends along the blue axis (in FIG. 2) and the red axis is less than 0.01% and the flexure joint experiences almost linear stiffness in bending (~1% increase from 0 degrees to 45 degrees). The effective torsional spring rate is 0/632 Nm/rad.

Figure 4:
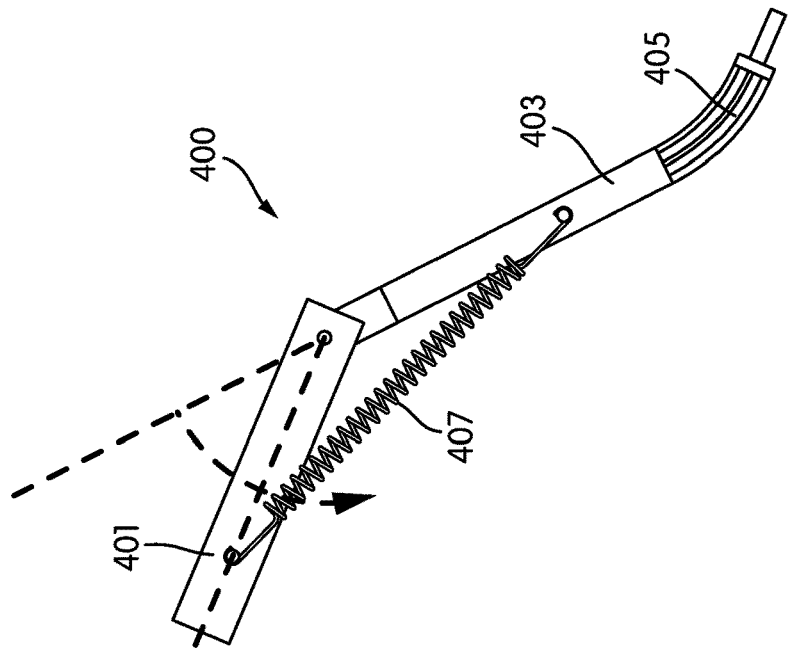
FIG. 4 is a perspective view of a manually actuated surgical tool including an energy balance mechanism.

FIG. 4 illustrates an example of a manually actuated surgical tool 400 that is similar to the tool 100 illustrated in FIG. 1. The surgical tool 400 includes a flex joint control handle 401, a hollow shaft 403, and a flexure joint 405 positioned at the distal end of the hollow shaft 403. The flex joint control handle 401 of the surgical tool 400 is only able to move about a single axis and, therefore, one moves with one degree of freedom. Therefore, the flexure joint 405 is also limited to movement with one degree of freedom. The surgical tool 400 also includes a spring 407 coupled to the flex joint control arm 401 and the hollow shaft 403. As discussed above, deformation of the flexure joint 405 and holding the flexure joint 405 in a deformed position requires constant force on the flex joint control arm 401. However, the spring 407 counteracts the elasticity of the joint and reduces (or eliminates) the force required to move the joint and hold the joint in a deformed position.

Figure 5:
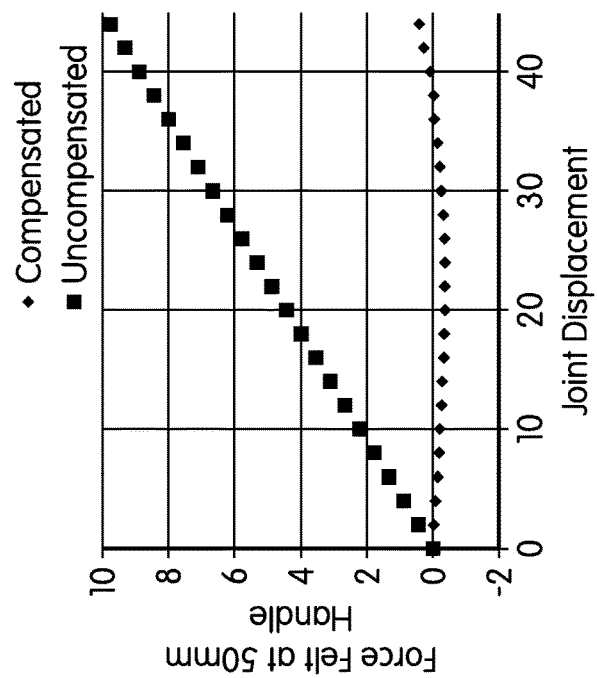
FIG. 5 is a graph of forces required to deform the flexure joint of the surgical tool of FIG. 1 and the flexure joint of the surgical tool of FIG. 4.

FIG. 5 illustrates the force required to move the flexure joint as a function of the total displacement of the flexure joint. The graph illustrates the difference between the force required to move the uncompensated flexure joint of FIG. 1 compared to the compensated flexure joint of FIG. 4. As shown in FIG. 5, the required force increases linearly in the uncompensated system. However, the force required to move the joint in the compensated system remains at (or, in some cases, below) zero.

Figure 6:
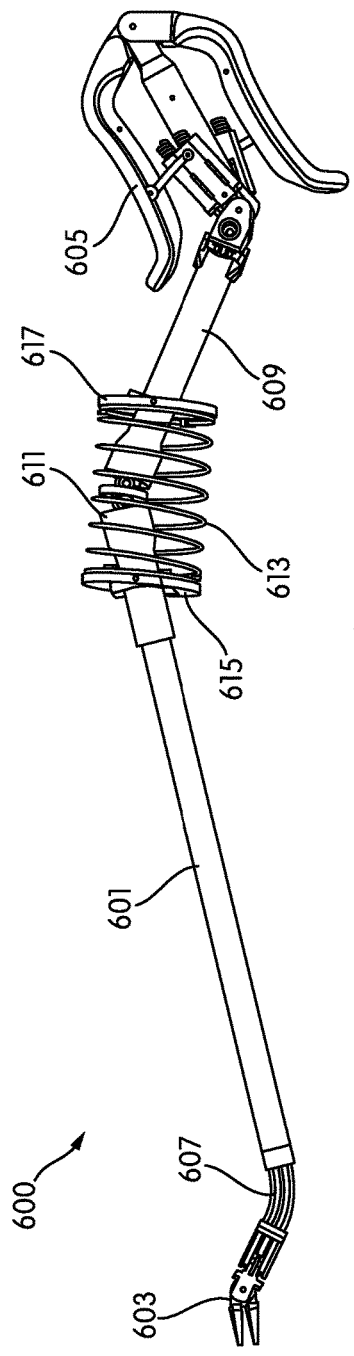
FIG. 6 is a perspective view of a surgical tool including an energy balance mechanism that includes a single spring.

FIG. 6 illustrates another example of a surgical tool 600 with a compensated flexure joint that provides for movement with two degrees of freedom. The surgical tool 600 includes a hollow shaft 601 with a gripper 603 at the distal end and an end effector control handle 605 at the opposite end. A flexure joint 607 is provided between the gripper 603 and the hollow shaft 601. A flex joint control arm 609 is coupled to the hollow shaft 601 by a control joint 611. The energy balance compensation is provided by a spring 613 mounted over the control joint 611 such that the control joint 611 operates inside the spring 613. The ends of the spring 613 are attached to gimbals 615, 617 mounted on either end of the control joint 611. The gimbals 615, 617 are linearly fixed to the end of the hollow shaft 601 and the flex joint control arm 609. However, the gimbals 615, 617 are configured to pivot such that the pull of the spring 613 keeps the gimbals 615, 617 substantially parallel with each other to prevent bending of the spring as the control joint 611 is actuated.

The spring 613 applies its force along the centerline of the hollow shaft 601 and the flex joint control arm 609. As with the one degree of freedom example of FIG. 4, the spring 613 provides force compensation as the control joint 611 is bent to overcome the elasticity of the flexure joint 607.

Figure 7:
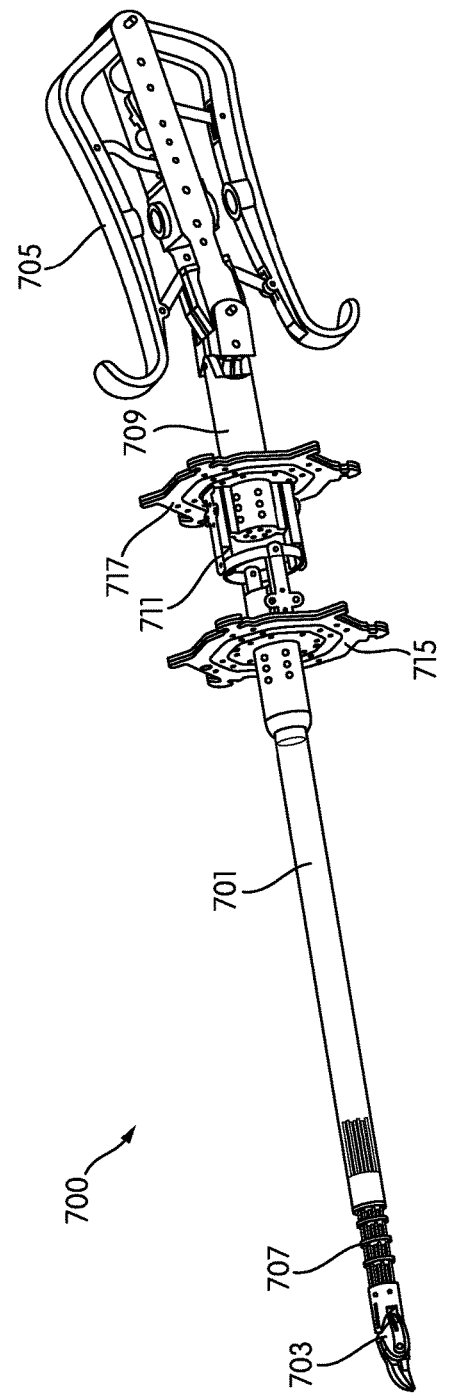
FIG. 7 is a perspective view of a surgical tool including an energy balance mechanism with the spring(s) removed to show the details of the gimbal structures.

FIG. 7 illustrates another example of a compensated surgical tool 700 with the springs removed to further illustrate the detail of the gimbals and the control joint. The surgical tool 700 includes a hollow shaft 701 with a gripper 702 at the distal end and an end effector control handle 705 at the proximal end. A flexure joint 707 is provided between the hollow shaft 701 and the gripper 703 while a flex joint control arm 709 is coupled to the hollow shaft 701 by a control joint 711. A pair of gimbals 715, 717 are provided on either side of the control joint 711.

Although the example of FIG. 6 (discussed above) utilizes a single spring wrapped around the control joint 611, it is possible to implement an energy balance mechanism with different spring arrangement. For example, the surgical tool 700 is designed to utilize three springs 813 that couple the first gimbal 715 to the second gimbal 717 on either end of the control joint 711. Although the springs 813 are omitted from the drawing of FIG. 7, FIG. 8 provides a more detailed view of the control joint and gimbal arrangement including the three springs 813.

Figure 8:
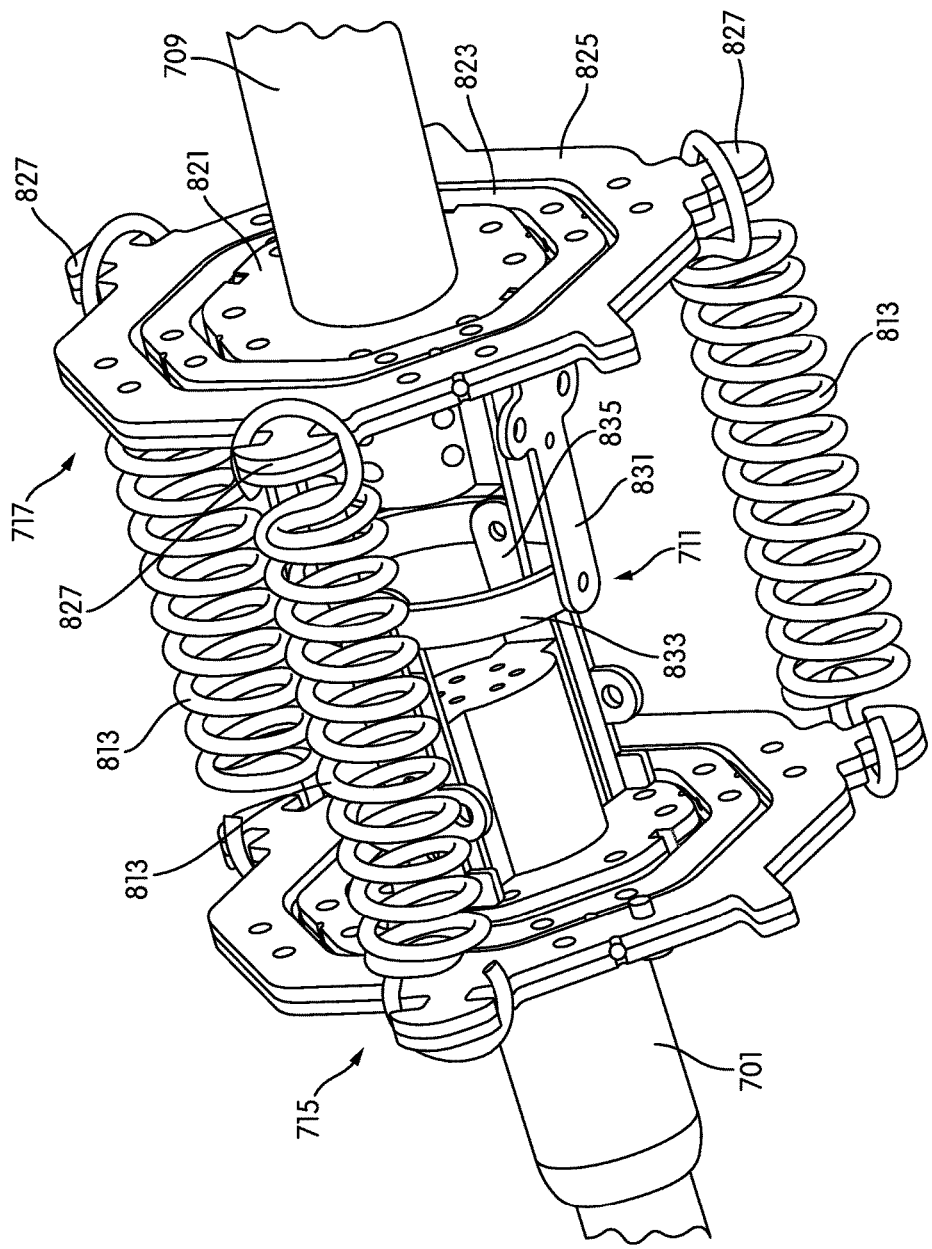
FIG. 8 is a detailed view of the control joint of the surgical tool of FIG. 7.

As shown in FIG. 8, the first gimbal 715 and the second gimbal 717 are each formed of a three piece structure. An inner ring 821 is fixedly attached to the flex joint control arm 709. A middle ring 823 is coupled to the inner ring 821 at two points to allow the middle ring 823 to pivot relative to the inner ring 821 on a first pivot axis. Similarly, an outer ring 825 is coupled to the middle ring 823 at two points to allow the outer ring 825 to pivot relative to the middle ring 823 on a second pivot axis. The points of connection between the middle ring 823 and the outer ring 825 are positioned such that the second pivot axis is perpendicular to the first pivot axis (i.e., the pivot axis between the middle ring 823 and the inner ring 821). The outer ring 825 also includes a series of three spring anchor points 827 positioned at regular intervals around the circumference of the ring.

Although not specifically labeled in FIG. 8, the first gimbal 715 in this example includes the same three-piece ring structure and a series of three corresponding spring anchor points as the second gimbal 717. Each spring 813 couples one anchor point 827 of the second gimbal 717 to a corresponding anchor point of the first gimbal 715. As a result, the springs provide a force that keeps the outer ring of the first gimbal 715 substantially parallel to the outer ring 825 of the second gimbal 717 regardless of the bend angle of the control joint 711. The three balance springs 813 in this arrangement kinematically act as a single spring to provide force compensation to counter act the elastic force of the deformed flexure joint 707. As described above, this force provides a counterbalance to the force required to deform the control joint (more specifically, to counterbalance the force required to deform the secondary tubes of the continuum shaft).

As discussed in detail above, the secondary tubes of the continuum shaft are relatively resistant to bending. However, when bending does occur, excessive force can cause the secondary tubes to break. Therefore, the control joint mechanisms of the surgical tool 700 provides a third gimbal structure that maintains a degree of separation between the first gimbal 715 and the second gimbal 717 and prevents the spring force (from springs 813) from causing the secondary tubes of the continuum shaft to break. The third gimbal in this example of FIG. 8 is positioned at the center of the control joint 711. A first pair of spacers 831 is fixedly connected to the stationary inner ring 821 of the second gimbal 717. The other end of each spacer is pivotally coupled to a central joint gimbal ring 833. This arrangement allows the central joint gimbal ring to pivot relative to the flex joint control arm 709. Similarly, a second pair of spacers 835 is fixedly coupled to the inner ring of the first gimbal 715 and pivotally coupled to central joint gimbal ring 833. The second pair of spacers 835 is positioned such that the pivot axis between the hollow shaft 701 and the central joint gimbal ring 833 is substantially perpendicular to the pivot axis between the flex joint control arm 709 and the central joint gimbal ring 833.

Figure 9:
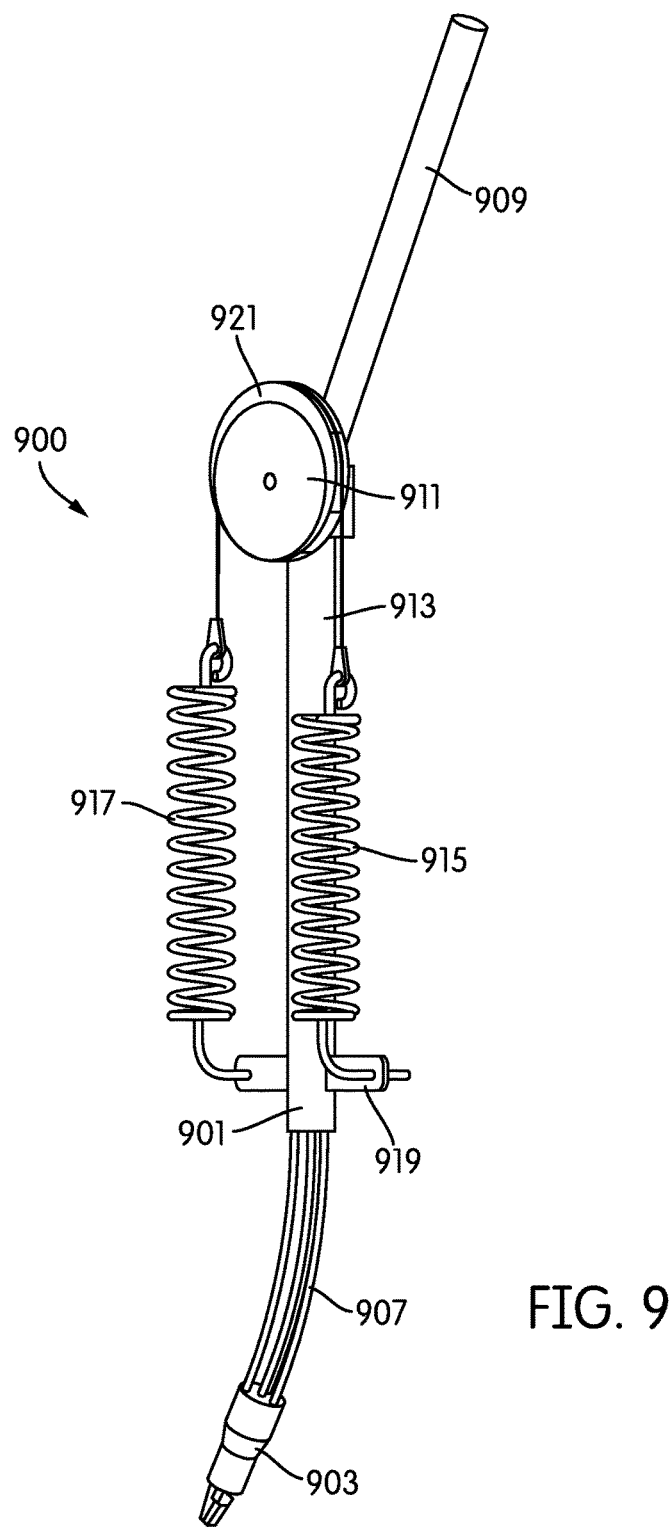
FIG. 9 is a perspective view of a surgical tool including a cam/pulley energy balance mechanism.

FIG. 9 illustrates yet another example of a surgical tool 900 with a counterbalance joint to compensate for the force required to deform the continuum shaft at the control joint. The surgical tool 900 includes a hollow shaft 901 and gripper end effector 903 with a flexure joint 907 between them. Like the other examples described above, a flexure joint control arm 909 is moveable relative to the hollow shaft 901 at a control joint and, thereby, causes a corresponding movement of the flexure joint 907. However, the flexure joint control arm 909 is only pivotable upon a single axis (i.e., left-to-right and right-to-left in FIG. 9).

A cam wheel 911 is positioned at the control joint. It is fixedly coupled to the control arm 909 and, therefore, pivots with the control arm 909 relative to the hollow shaft 901. A cable 913 wraps around the outer surface of the cam 911 with each end coupled to a spring 915, 917. The opposite end of each spring 915, 917 is coupled to an anchor point 919 which is fixedly coupled to the hollow shaft 901. The cam wheel 911 is shaped and positioned such that one surface 921 has a larger radius than the others. This enlarged radius surface 921 is positioned such that it is facing away from the end effector 903 when the control arm 909 is at a centered position. As a result, the spring force provided by the springs 915, 917 is the greatest when the control arm 909 is centered and the cam profile works to move the handle away from centered. As the control arm 909 is pivoted, the cam wheel 911 rotates and the effective pulley diameters are changed. Thus, the two springs 915, 917 are balanced when the control arm 909 is centered. When the control arm 909 is deflected, one cam increases in diameter and thus pulls harder on the lever as compared to the other cam. The cam wheel 911 is sized and the springs 915, 917 are selected such that the increase in cam diameter overcomes the decrease in spring force as the spring stretch is decreased.

Figure 10:
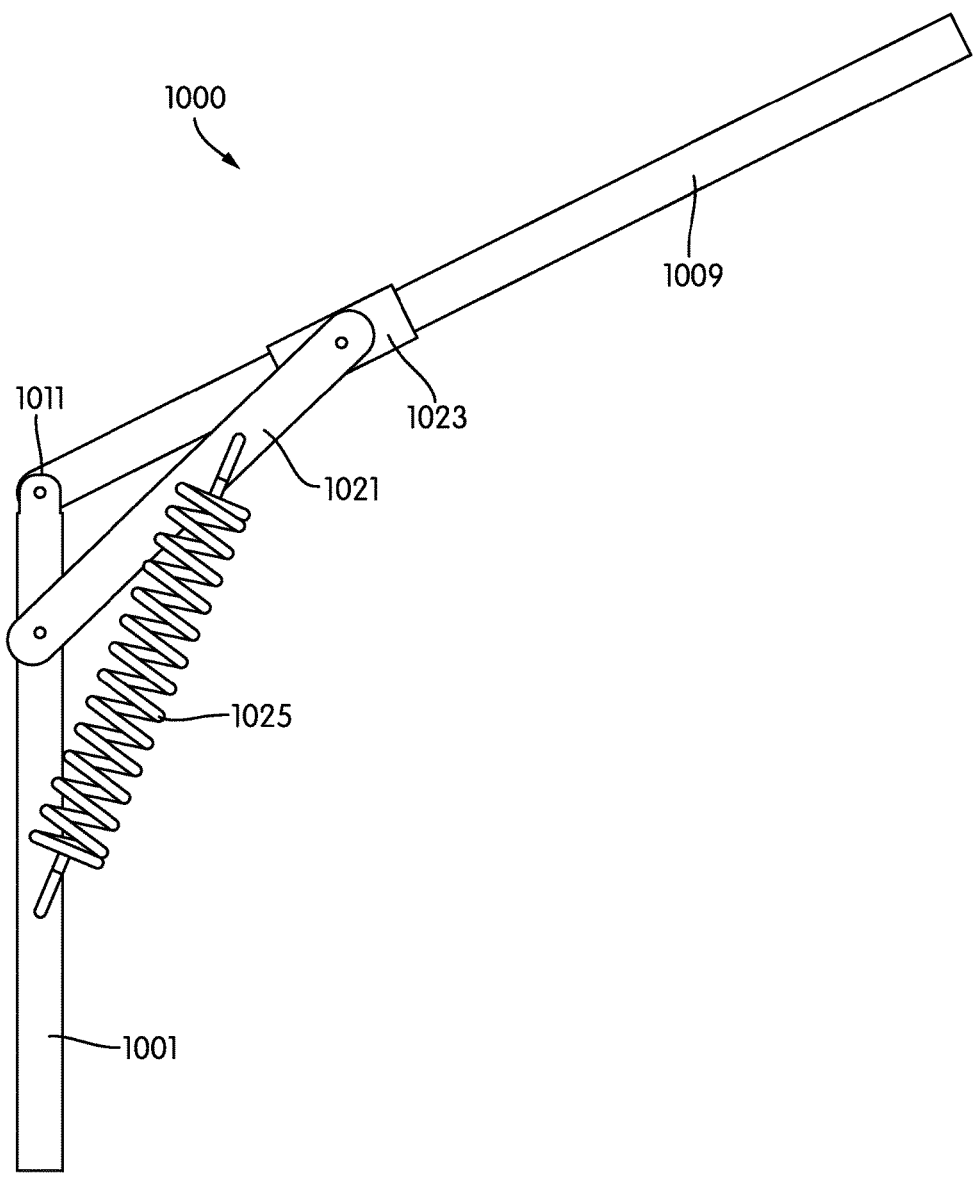
FIG. 10 is a perspective view of a surgical tool including a sliding link energy balance mechanism.

FIG. 10 illustrates still another example of a surgical tool 1000 with a counterbalance joint to compensate for the force required to deform the continuum shaft at the control joint. The surgical tool 1000 includes a hollow shaft 1001, a gripper end effector (not shown), and a flexure joint (not shown) between the hollow shaft 1001 and the end effector. A flexure joint control arm 1009 is pivotally coupled to the hollows shaft 1001 at a control joint 1011. A coupling link 1021 is pivotally connected to the hollow shaft 1001 at one end and coupled to a slider 1023 at the other. The slider 1023 allows the end of the coupling link 1021 to move up and down the length of the control arm 1009 as the control arm 1009 is pivoted relative to the hollow shaft 1001. A spring 1025 is coupled between the coupling link 1021 and another point on the hollow shaft 1011.

In this example, the spring 1025 is coupled to the hollow shaft 1001 at a point that is further from the control joint 1011 than the point of coupling between the coupling link 1021 and the hollow shaft 1001. Therefore, the length of the spring 1025 decreases as the control joint 1011 is further deflected. As a result, the force provided by the spring 1025 pulls the control arm 1009 away from center and counter balances the force required to deform the secondary tubes of the continuum shaft.

Thus, the invention provides, among other things, an energy balance mechanism for a flexure joint that counteract the elastic force caused by deformation of the flexure joint. Various features and advantages of the invention are set forth in the following claims.

What is claimed is:

1. A tool comprising:
   a hollow shaft;
   a flex joint control arm pivotally coupled to the hollow shaft;
   an elastically deformable flexure joint;
   a control joint that is mechanically linked to the flexure joint such that movement of the control joint via the flex joint control arm causes a corresponding deformation of the flexure joint;
   an energy balance system that provides a counter force to aid movement of the control joint and to overcome a force required to deform the flexure joint, wherein the energy balance system includes a spring having a first end coupled to the flex joint control arm and a second opposite end coupled to the hollow shaft; and
   a continuum shaft positioned through the hollow shaft, wherein a portion of the continuum shaft extending from a first end of the hollow shaft forms the flexure joint and a portion of the continuum shaft extending from a second end of the hollow shaft forms the control joint,
   wherein the continuum shaft includes a central backbone and a plurality of parallel tubes arranged around the central backbone, the plurality of parallel tubes being fixedly attached to the central backbone at a first end of the continuum shaft and at a second end of the continuum shaft,
   wherein the plurality of parallel tubes are independently linearly moveable through the hollow shaft relative to the central backbone such that bending the control joint extends a first tube of the plurality of parallel tubes through the hollow shaft and retracts a second tube of the plurality of parallel tubes through the hollow shaft, and
   wherein the extension of the first tube and the retraction of the second tube causes the flexure joint to bend.

2. The tool of claim 1, wherein the energy balance system further includes
   a first gimbal positioned at a first end of the flexure joint;
   a second gimbal positioned at a second end of the flexure joint opposite the first gimbal; and a spring coupled to the first gimbal and the second gimbal to provide the counter force to aid movement of the control joint and to overcome the force required to deform the flexure joint.

3. The tool of claim 2, wherein the first gimbal includes a fixed stage and a pivoting stage, wherein the second gimbal includes a fixed stage and a pivoting stage, and wherein the spring is coupled to the pivoting stage of the first gimbal and the pivoting stage of the second gimbal such that the pivoting stage of the first gimbal remains substantially parallel to the pivoting stage of the second gimbal regardless of the movement of the control joint.

4. The tool of claim 2, further comprising a second spring and a third spring, wherein the second spring and the third spring are both coupled to the first gimbal and the second gimbal, and wherein the spring, the second spring, and the third spring are arranged around the control joint such that the counter force is applied substantially along a centerline of the control joint.

5. The tool of claim 1, wherein, when the control joint is bent in a first direction, the corresponding deformation of the flexure joint includes a bending of the flexure joint in the first direction.

6. The tool of claim 1, wherein, when the control joint is bent at a first angle, the corresponding deformation of the flexure joint includes a bending of the flexure joint at a magnitude proportional to the first angle.

7. The tool of claim 1, wherein, when the control joint is bent in a first direction, the corresponding deformation of the flexure joint includes a bending of the flexure joint in an opposite direction.

8. The tool of claim 1, further comprising an end effector coupled to the flexure joint such that deformation of the flexure joint causes the end effector to pivot.

9. The tool of claim 1, further comprising
an end effector coupled to the flexure joint; and
a control handle coupled to the flexure joint control arm, wherein manipulation of the control handle controls the operation of the end effector.

10. The tool of claim 9, wherein the end effector includes a wrist joint, and wherein the control handle includes a wrist control joint configured to control a bending of the wrist joint of the end effector.

11. The tool of claim 9, wherein the end effector includes a gripper, wherein the control handle includes at least one moveable lever, and wherein the control handle is configured such that movement of the at least one moveable lever cause the gripper to open and close.

12. A surgical tool comprising:
a hollow shaft;
an end effector coupled to a distal end of the hollow shaft by an elastically deformable flexure joint;
a joint control arm coupled to a proximal end of the hollow shaft by a control joint, the control joint being mechanically coupled to the flexure joint such that movement of the control joint causes a corresponding deformation of the flexure joint;
an energy balance system that provides a counter force to aid movement of the control joint and to overcome a force required to deform the flexure joint, wherein the energy balance system includes a spring having a first end coupled to the joint control arm and a second opposite end coupled to the hollow shaft; and
a continuum shaft positioned through the hollow shaft and coupled to the end effector and the joint control arm, wherein the continuum shaft includes a central backbone and a plurality of parallel tubes arranged around the central backbone, wherein the plurality of parallel tubes are linearly moveable relative to the central backbone, wherein the flexure joint is formed of a portion of the continuum shaft, and wherein linear movement of the plurality of parallel tubes relative to the central backbone causes deformation of the flexure joint.

13. The surgical tool of claim 12, wherein bending the control joint extends a first tube of the plurality of parallel tubes through the hollow shaft and retracts a second tube of the plurality of parallel tubes through the hollow shaft, and wherein the extension of the first tube and the retraction of the second tube causes the flexure joint to bend.

14. The surgical tool of claim 12, wherein the energy balance system further includes
a first gimbal positioned at a first end of the flexure joint;
a second gimbal positioned at a second end of the flexure joint opposite the first gimbal; and
a spring coupled to the first gimbal and the second gimbal to provide the counter force to aid movement of the control joint and to overcome the elastic force required to deform the flexure joint.

15. The surgical tool of claim 14, wherein the first gimbal includes a fixed stage and a pivoting stage, wherein the second gimbal includes a fixed stage and a pivoting stage, and wherein the spring is coupled to the pivoting stage of the first gimbal and the pivoting stage of the second gimbal such that the pivoting stage of the first gimbal remains substantially parallel to the pivoting stage of the second gimbal regardless of the movement of the control joint.

16. The surgical tool of claim 14, further comprising a second spring and a third spring, wherein the second spring and the third spring are both coupled to the first gimbal and the second gimbal, and wherein the spring, the second spring, and the third spring are arranged around the control joint such that the spring force is applied substantially along a centerline of the control joint.

* * * * *